United States Patent
Hamilton, II et al.

(10) Patent No.: US 10,216,909 B2
(45) Date of Patent: Feb. 26, 2019

(54) HEALTH MONITORING

(71) Applicant: INTERNATIONAL BUSINESS MACHINES CORPORATION, Armonk, NY (US)

(72) Inventors: Rick A. Hamilton, II, Charlottesville, VA (US); James R. Kozloski, New Fairfield, CT (US); Brian M. O'Connell, Cary, NY (US); Ninad D. Sathaye, Pune (IN)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 58 days.

(21) Appl. No.: 15/184,257

(22) Filed: Jun. 16, 2016

(65) Prior Publication Data

US 2017/0365048 A1 Dec. 21, 2017

Related U.S. Application Data

(63) Continuation of application No. 15/183,236, filed on Jun. 15, 2016.

(51) Int. Cl.
*G06F 19/00* (2018.01)
*G16H 10/60* (2018.01)
(Continued)

(52) U.S. Cl.
CPC ........ *G06F 19/3481* (2013.01); *A61B 5/0022* (2013.01); *A61B 5/01* (2013.01); *A61B 5/024* (2013.01); *A61B 5/1112* (2013.01); *A61B 5/1118* (2013.01); *A61B 5/486* (2013.01); *A61B 5/4866* (2013.01); *A61B 5/681* (2013.01); *G06F 17/30528* (2013.01); *G06F 19/00* (2013.01);
(Continued)

(58) Field of Classification Search
CPC combination set(s) only.
See application file for complete search history.

(56) References Cited

U.S. PATENT DOCUMENTS

| 8,814,671 B2 * | 8/2014 | Bhogal | G08B 21/02 |
| | | | 463/29 |
| 2013/0027060 A1 * | 1/2013 | Tralshawala | G01N 22/04 |
| | | | 324/643 |

(Continued)

OTHER PUBLICATIONS

List of IBM Patents or Patent Applications Treated as Related; (Appendix P), Filed Jan. 17, 2017; 2 pages.

(Continued)

*Primary Examiner* — Tsung Yin Tsai
(74) *Attorney, Agent, or Firm* — Cantor Colburn LLP; Rahan Uddin

(57) ABSTRACT

Technical solutions are described for monitoring health of a user by a healthcare system. An example computer-implemented method includes accessing a current image of the user. The computer-implemented method also includes determining a healthcare routine for the user. The computer-implemented method also includes generating a modified image of the user, where the modified image includes a predicted effect of the healthcare routine. The computer-implemented method also includes displaying, for viewing by the user, the modified image, and information about the healthcare routine.

19 Claims, 12 Drawing Sheets

(51) Int. Cl.
  *A61B 5/11* (2006.01)
  *A61B 5/00* (2006.01)
  *G06F 17/30* (2006.01)
  *G06K 9/46* (2006.01)
  *G06T 7/00* (2017.01)
  *H04N 5/33* (2006.01)
  *A61B 5/01* (2006.01)
  *A61B 5/024* (2006.01)

(52) U.S. Cl.
  CPC .......... *G06F 19/321* (2013.01); *G06F 19/328* (2013.01); *G06K 9/4604* (2013.01); *G06T 7/0004* (2013.01); *G16H 10/60* (2018.01); *H04N 5/332* (2013.01); *G06T 2207/30128* (2013.01)

(56) References Cited

U.S. PATENT DOCUMENTS

| | | | |
|---|---|---|---|
| 2014/0185046 A1* | 7/2014 | Urushidani | G01N 21/359 356/402 |
| 2014/0240508 A1* | 8/2014 | Gomi | G01J 3/2823 348/162 |
| 2014/0240711 A1* | 8/2014 | Matsushita | G01J 3/0205 356/451 |
| 2014/0349256 A1* | 11/2014 | Connor | G09B 19/0092 434/127 |
| 2015/0168365 A1* | 6/2015 | Connor | G01N 33/02 356/51 |
| 2015/0189139 A1* | 7/2015 | Funamoto | G01J 3/26 348/222.1 |
| 2015/0204832 A1* | 7/2015 | Ochi | G01N 21/3554 702/30 |
| 2015/0281535 A1* | 10/2015 | Korenaga | G01N 33/025 348/360 |
| 2015/0318799 A1* | 11/2015 | Hirokubo | G05B 11/14 359/584 |
| 2016/0012749 A1* | 1/2016 | Connor | G09B 5/00 600/13 |
| 2016/0034764 A1* | 2/2016 | Connor | G06K 9/00771 348/158 |
| 2016/0057330 A1* | 2/2016 | Zhao | H04N 5/2353 348/222.1 |
| 2016/0148536 A1* | 5/2016 | Ashby | G09B 19/0092 434/127 |
| 2016/0150213 A1* | 5/2016 | Mutti | G01N 33/02 348/143 |
| 2016/0260352 A1* | 9/2016 | Ortiz | G09B 19/0092 |
| 2017/0249445 A1* | 8/2017 | Devries | G16H 10/60 |

OTHER PUBLICATIONS

Rick A. Hamilton et al., "Health Monitoring", U.S. Appl. No. 15/183,236, filed Jun. 15, 2016.

* cited by examiner

HEALTH MONITORING

DOMESTIC PRIORITY

This application is a continuation of and claims priority from U.S. patent application Ser. No. 15/183,236, filed on Jun. 15, 2016, entitled "HEALTH MONITORING," the entire contents of which are incorporated herein by reference.

BACKGROUND

The present application relates to healthcare, and more specifically, to using computer technology to provide personalized healthcare suggestions based on healthcare records and ongoing healthcare monitoring.

Sedentary lifestyles and easy availability of low cost, high-energy food are contributing factors for obesity. Obesity related health issues cause strain on insurance and healthcare providers. It has been estimated that the cost of obesity related healthcare expenses in the United States alone is $190 billion dollars.

SUMMARY

According to one or more embodiments, a computer implemented method for monitoring a health of a user by a healthcare system includes accessing a current image of the user. The computer implemented method also includes determining a healthcare routine for the user. The computer implemented method also includes generating a modified image of the user, where the modified image includes a predicted effect of the healthcare routine. The computer implemented method also includes displaying, for viewing by the user, the modified image and information about the healthcare routine.

According to one or more embodiments, a system for monitoring a health of a user includes a communication interface; a memory; and a processor coupled with the memory and the communication interface. The processor accesses a current image of the user. The processor further generates a healthcare routine for the user. The processor further generates a modified image of the user, where the modified image includes a predicted effect of the healthcare routine. The processor also displays, for viewing by the user, the modified image, and information about the healthcare routine.

According to one or more embodiments, a computer program product for monitoring a health of a user includes a non-transitory computer readable storage medium. The computer readable storage medium includes computer executable instructions to access a current image of the user. The computer readable storage medium also includes instructions to generate a healthcare routine for the user. The computer readable storage medium also includes instructions to generate a modified image of the user, where the modified image includes a predicted effect of the healthcare routine. The computer readable storage medium also includes instructions to display, for viewing by the user, the modified image and the healthcare routine.

According to one or more embodiments, a system for monitoring a health of a user includes an image capture device configured to capture multispectral images. The system further includes a memory; and a processor coupled with the memory and the image capture device. The processor captures a multispectral image of a food-item. The processor also determines a caloric-value of the food-item based on the multispectral image of the food-item, and outputs the caloric-value of the food-item.

According to one or more embodiments, a computer program product for monitoring a health of a user includes a non-transitory computer readable storage medium. The computer readable storage medium includes computer executable instructions to capture a multispectral image of a food-item. The computer readable storage medium also includes instructions to determine a caloric-value of the food-item based on the multispectral image of the food-item, and output the caloric-value of the food-item.

According to one or more embodiments, a computer-implemented method for monitoring a health of a user includes determining a caloric-value of a food-item based on a multispectral image of the food-item. The method further includes outputting the caloric-value of the food-item.

BRIEF DESCRIPTION OF THE DRAWINGS

The examples described throughout the present document may be better understood with reference to the following drawings and description. The components in the figures are not necessarily to scale. Moreover, in the figures, like-referenced numerals designate corresponding parts throughout the different views.

DETAILED DESCRIPTION

Figure 1:
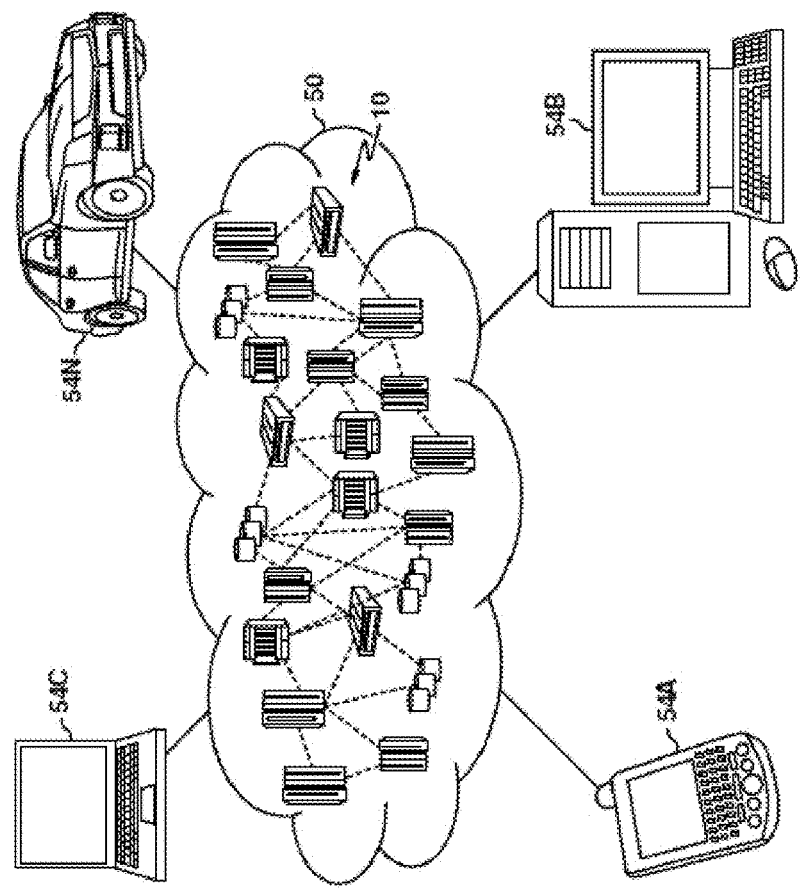
FIG. 1 illustrates a cloud computing environment in accordance with one or more embodiments.

Example embodiments of the disclosure include or yield various technical features, technical effects, and/or improvements to technology. For instance, example embodiments of the disclosure provide the technical effect of analyzing health records and activity tracking data of one or more individuals for determining an ability of the individuals to perform exercise, and suggesting an exercise and/or dietary routine for the individuals based on the ability and a variety of factors, such as a location, a schedule, among others, of the individuals. This technical effect is achieved as a result of the technical features of gathering of data on the progress of the individuals using one or more wearable computing devices, and analyzing the data to provide visual portrayal of the progress the individuals have made over a period of time based on following a health-routine. For example, the technical solutions include determining the health-routine for a user based on the user's health records and activity tracking data. The technical solutions further include accessing a current image of the user, and generating a modified image of the user that predicts an effect of the user following the health-routine. The images referred to in the above example, and throughout the present document, include digital images, such as those captured by a camera and stored in non-transitory computer readable storage medium. The technical features further include tracking activity data of the user via wearable computing devices, and using the activity data to generate the modified image.

In one or more examples, the technical effects of the technical solutions include identifying one or more exercise routines for the user based on a geographic location of the user. For example, the technical features may include identifying a parking location that facilitates the user to take at least a predetermined number of steps to enter his/her workplace or any other location. In one or more examples, the technical features include displaying a progress report for viewing by the user, the progress report including the current image, a first modified image, and a second modified image, where the first modified image is a predicted image after completing the health-routine, and the second modifies image is a predicted image based on current activity data used to modify the current image of the user. As a result of the aforementioned technical features and technical effects, example embodiments of the disclosure constitute an improvement to existing health-monitoring computing technology. It should be appreciated that the above examples of technical features, technical effects, and improvements to technology of example embodiments of the disclosure are merely illustrative and not exhaustive.

Example embodiments of the disclosure include or yield various technical features, technical effects, and/or improvements to technology. Example embodiments of the disclosure provide a health monitoring system that generates a modified image of a user, where the modified image includes a predicted effect on a current image of the user. The predicted effect is based on the user following a health routine identified specifically for the user. The technical features of the example embodiments further include tracking activity data of the user, such as exercise and diet, via wearable computing devices and other monitoring apparatus. The activity data facilitates generating additional modified images that visually portray an effect of the health routine on a physical form of the user. One or more examples may further include the technical features of sharing the progress data/information with healthcare providers. The technical solutions may further facilitate providing the progress information with other stakeholders, such as insurance providers. As a result of these technical features and technical effects, a health monitoring system in accordance with example embodiments of the disclosure represents an improvement to existing health monitoring techniques. It should be appreciated that the above examples of technical features, technical effects, and improvements to technology of example embodiments of the disclosure are merely illustrative and not exhaustive.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
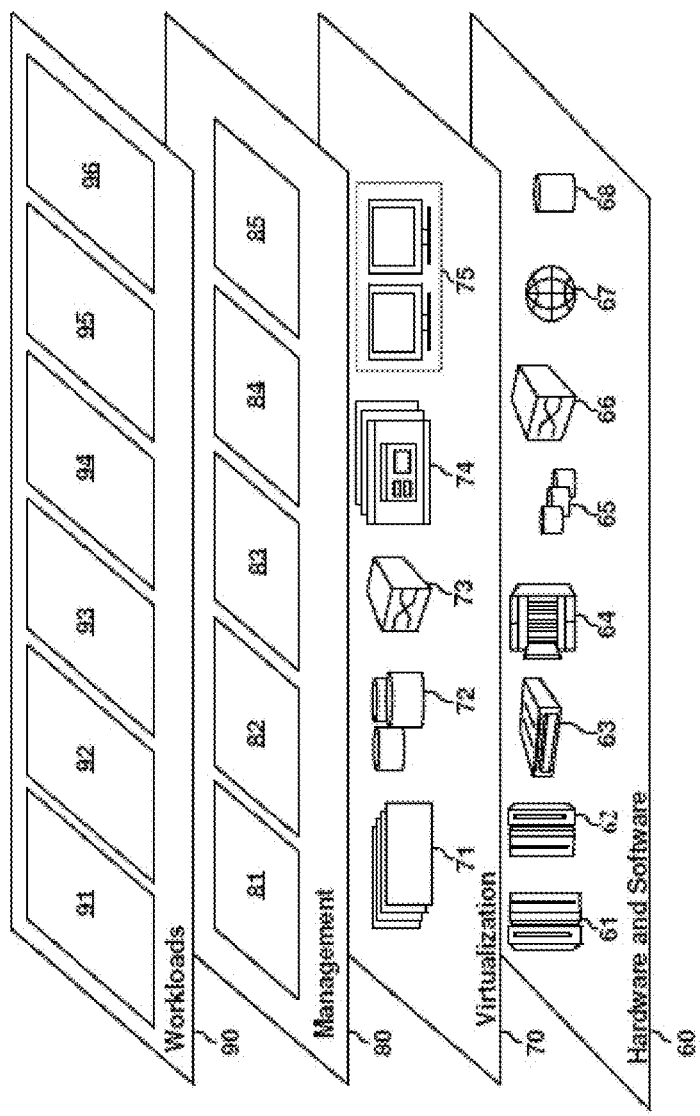
FIG. 2 illustrates a set of functional abstraction layers provided by cloud computing environment in accordance with one or more embodiments.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing and analysis of customer feedback of applications 96.

Figure 3:
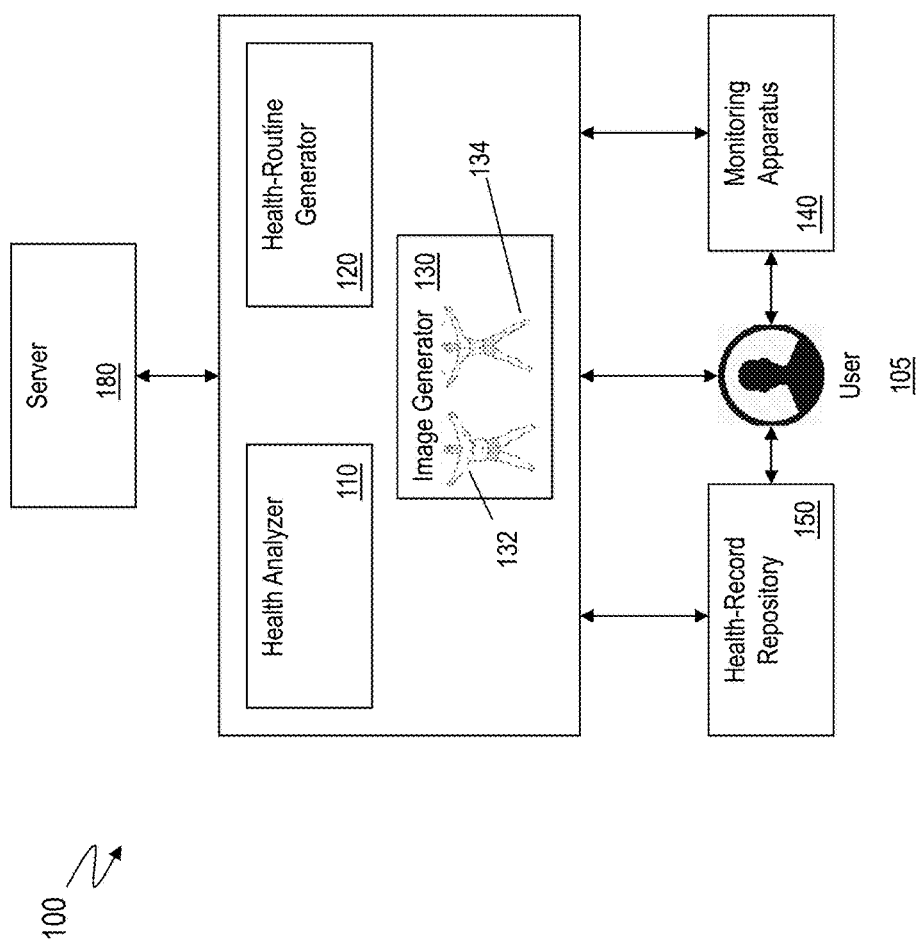
FIG. 3 illustrates an example healthcare system in accordance with one or more embodiments.

FIG. 3 illustrates an example healthcare system 100 that implements the technical solutions described herein. The healthcare system 100 includes multiple components in communication with each other. For example, the components may include a health-record analyzing unit 110, a health-routine generator unit 120, and an image generator unit 130. The healthcare system 100 may further include a monitoring apparatus 140 and a health-record repository 150. Although FIG. 1 illustrates the components separately, it is understood that the components may be organized in a different manner. For example, the healthcare system 100 may include fewer or more components than illustrated. Alternatively or in addition, the healthcare system 100 may include a component that performs operations of a combination of the components illustrated in FIG. 1. The healthcare system 100 may be in communication with one or more external servers such as a server 180. The healthcare system 100 facilitates analyzing and monitoring the health of a user 105. In one or more examples, the healthcare system 100 facilitates analyzing and monitoring the health of more than one user.

The health-record analyzing unit 110 analyzes the user's (105) records. For example, health-record analyzing unit 110 determines if the user 105 is overweight and/or has limitations such as physical disabilities or health conditions that may impact the user's ability to perform specific exercise or dietary routines. For example, if the user's health-record indicates that the user 105 has previously complained of, or been diagnosed with a knee (or any other body-part) problem, the health-record analyzing unit 110 identifies that the user 105 has a limitation with exercises that may require the user 105 to strain the knee (or any other body-part). The health-record analyzing unit 110 shares such information with the other components of the healthcare system 100, such as the healthcare-routine generator unit 120 to prevent proposing running as an exercise routine.

The health-record analyzing unit 110 accesses the health-record(s) for the user 105 from the health-record repository 150. The health-record repository 150 may be part of the health-record analyzing unit 110 in one or more examples. The health-record repository 150 may be a database that includes past health-records of the user 105. The health-records may include data collected during one or more doctor visits and/or laboratory visits. For example, the health-records may include electronic medical records that include health related data of the user 105 such as weight, height, glucose level, hemoglobin level, blood-cell counts, body-mass index, cholesterol level, and any other such biomedical measurements of the user 105. The health-records may further include allergy information for the user 105. The health-records may further identify if the user 105 has undergone a medical procedure such as a surgery. The health-records may, in such a case, include details of the medical procedure, such as the diagnosis, the prognosis, and specific treatment that was suggested to the user 105 because of the medical procedure. For example, the health-record may identify that the user 105 underwent a magnetic resonance imaging (MRI) scan of a knee, which identified an injury to the knee resulting in a surgical procedure of the knee. The health-record repository 150 may additionally include data from the monitoring apparatus 140.

The monitoring apparatus 140 may be an apparatus that monitors activity being performed by the user 105. For example, the monitoring apparatus 140 may be a wearable device, such as a watch, a fitness band, a pedometer, a smart-phone, or any other apparatus that includes one or more sensors to monitor the user 105. The monitoring apparatus 140 tracks physical activity and being performed by the user 105 and its effects on the user 105. For example, the monitoring apparatus 140 tracks a number of steps taken by the user 105, or a number of miles walked/run by the user 105, exercises performed by the user 105, or tracks any other such physical activity. The monitoring apparatus 140, alternatively or in addition, tracks a heart rate, calories burnt, and other such effects of the physical activity on the user 105.

In addition or alternatively, the monitoring apparatus 140 tracks food consumed by the user 105. For example, the user 105 may be prompted to enter data about the food that the user 105 consumes. For example, the user 105 enters the data via the monitoring apparatus 140. In one or more examples, the user 105 enters the data via another user-interface device (not shown). The data includes nutritional information about the food, such as the calories, and other nutritional information such as fat content, carbohydrate content, protein content, sugar content, vitamin content, and other such nutritional information. In one or more examples, the monitoring apparatus 140 scans information of the food being consumed by the user 105 by capturing an image or scanning a code associated with the food.

For example, if the user 105 is consuming the food at a restaurant or any other place of business, the food may be associated with a machine readable code, such as a quick-response (QR) code, a barcode, a uniform resource locator (URL) or any other identifier of the food. For example, a receipt or a menu from the restaurant may include the machine readable code providing details of nutritional information served. In yet another embodiment, the user 105 takes a picture of the food, such as on the plate and the healthcare system 100 determines the nutritional information of the food, for example by comparing the image with other images with known nutritional information. Alternatively or in addition, the healthcare system 100 determines the nutritional information using crowd-sourcing. For example, the healthcare system 100 sends the image of the food to a crowd-sourcing server, such as the external server 180, and in response receives an estimate of the nutritional information of the food from one or more users of the external server 180.

The monitoring apparatus 140 provides the sensor data, which includes the physical activity data and the nutritional information of the food being consumed by the user 105 to the healthcare system 100, in real-time in one or more examples.

The healthcare-routine generator unit 120 generates a health routine for the user 105 based on the health analysis by the health-record analyzing unit 110. In addition, the healthcare-routine generator unit 120 generates the health-routine based on the sensor data from the monitoring apparatus 140. The health routine includes an exercise routine and a dietary routine. For example, the exercise routine may include one or more exercises for the user 105 to perform. The exercise routine may further include a schedule to perform the exercises at a specific time, specific day, or a combination thereof. The exercise routine may further indicate a geographic location to perform the exercises. The dietary routine may indicate one or more food items for the user 105 to consume. The dietary routine may further include a schedule to consume the food items, such as a specific time, specific day, or a combination thereof. The dietary routine may further indicate one or more locations to obtain the food items from.

The image generator unit 130 generates a visual portrait or an image of the user 105. The visual portrait or the image includes one or more digital images of the user 105. The image generator unit 130 accesses a current image 132 of the user 105, and generates a modified image 134 that visually represents the effects of the user following the health routine suggested by the healthcare-routine generator unit 120. The modified image 134 may indicate a predicted appearance of the user 105 based on the predictions from the health-record analyzing unit 110. Alternatively, the modified image 134 may indicate a predicted appearance of the user 105 if the user 105 does not follow the healthcare routine and instead continues with a current routine. The modified image 134 may include changes to weight, BMI, fat/muscle composition, and also include an aging model, to reflect other components of the user's 105 health history and habits. For example, the image generator unit 130 may reflect the effects of smoking, alcohol consumption, sun exposure, and stress. The image generator unit 130 may generate the modified image 134 based on the health records from the health-record repository 150 and data from the monitoring apparatus 140. In an example, the image generator unit 130 provides a user-interactive element, such as a controller, a button, a dial, a text-box, a combo-box, or any user-interface element, for the user 105 to select a time in the future. The image generator unit 130 generates the modified image 134 that reflects the predictions for the user's 105 appearance at the selected time based on the health records and the sensor data.

Figure 4:
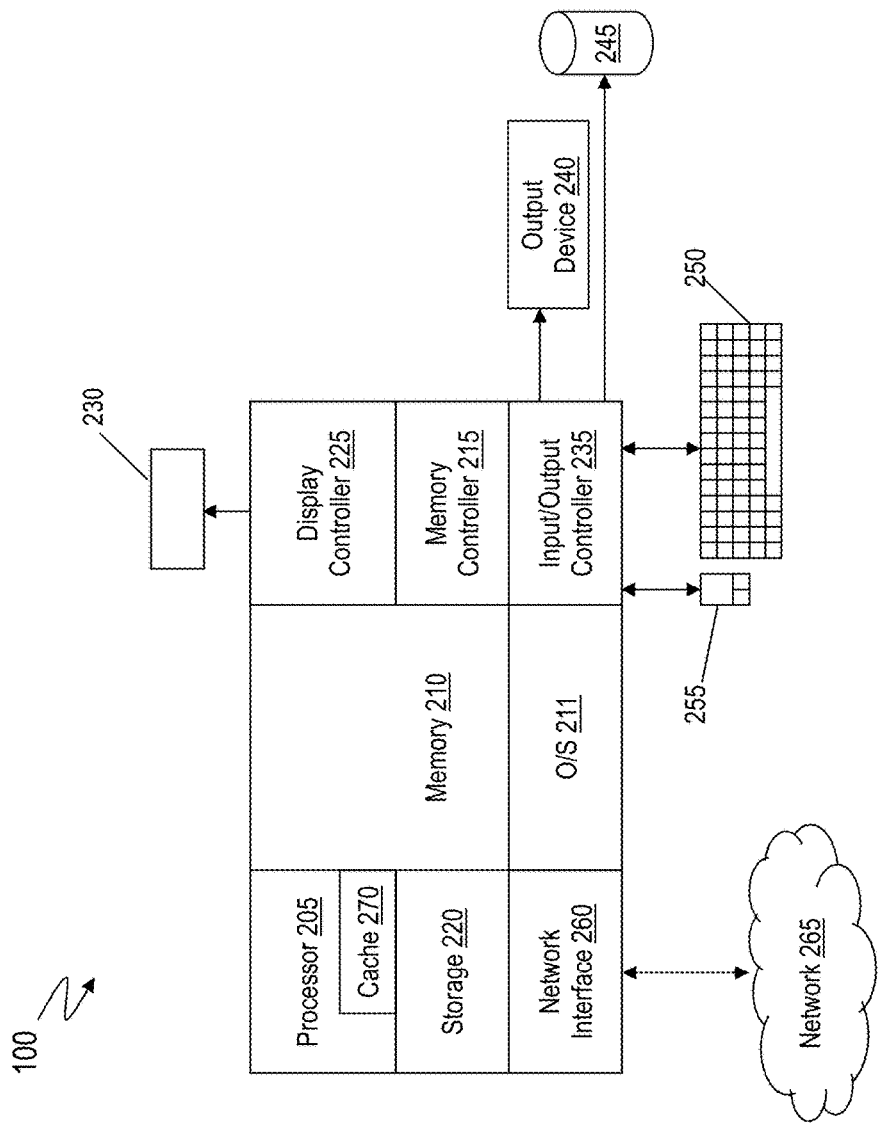
FIG. 4 illustrates example components of the healthcare system in accordance with one or more embodiments.

FIG. 4 illustrates example components of the healthcare system 100. The system 100 may be a communication apparatus, such as a computer. For example, the system 100 may be a desktop computer, a tablet computer, a laptop computer, a phone, such as a smartphone, a server computer, or any other device that communicates via a network 265. The system 100 includes hardware, such as electronic circuitry. In one or more examples FIG. 4 illustrates example components of each unit of the healthcare system 100, such as the health-record analyzing unit 110, the healthcare-routine generator unit 120, the image generator unit 130. Further, in one or more examples, the monitoring apparatus 140 also includes at least the components illustrated in FIG. 4. Further yet, the server 180 may be a computer server that includes at least the components illustrated in FIG. 4.

The system 100 illustrated in FIG. 4 includes, among other components, a processor 205, memory 210 coupled to a memory controller 215, and one or more input devices 245 and/or output devices 240, such as peripheral or control devices, that are communicatively coupled via a local I/O controller 235. These devices 240 and 245 may include, for example, battery sensors, position sensors (altimeter, accelerometer, global positioning system (GPS)), indicator/identification lights and the like. Input devices such as a conventional keyboard 250 and mouse 255 may be coupled to the I/O controller 235. The I/O controller 235 may be, for example, one or more buses or other wired or wireless connections, as are known in the art. The I/O controller 235 may have additional elements, which are omitted for simplicity, such as controllers, buffers (caches), drivers, repeaters, and receivers, to enable communications.

The I/O devices 240, 245 may further include devices that communicate both inputs and outputs, for instance disk and tape storage, a network interface card (NIC) or modulator/demodulator (for accessing other files, devices, systems, or a network), a radio frequency (RF) or other transceiver, a telephonic interface, a bridge, a router, and the like.

The processor 205 is a hardware device for executing hardware instructions or software, particularly those stored in memory 210. The processor 205 may be a custom made or commercially available processor, a central processing unit (CPU), an auxiliary processor among several processors associated with the system 100, a semiconductor based microprocessor (in the form of a microchip or chip set), a macroprocessor, or other device for executing instructions. The processor 205 includes a cache 270, which may include, but is not limited to, an instruction cache to speed up executable instruction fetch, a data cache to speed up data fetch and store, and a translation lookaside buffer (TLB) used to speed up virtual-to-physical address translation for both executable instructions and data. The cache 270 may be organized as a hierarchy of more cache levels (L1, L2, and so on.).

The memory 210 may include one or combinations of volatile memory elements (for example, random access memory, RAM, such as DRAM, SRAM, SDRAM) and nonvolatile memory elements (for example, ROM, erasable programmable read only memory (EPROM), electronically erasable programmable read only memory (EEPROM), programmable read only memory (PROM), tape, compact disc read only memory (CD-ROM), disk, diskette, cartridge, cassette or the like). Moreover, the memory 210 may incorporate electronic, magnetic, optical, or other types of storage media. Note that the memory 210 may have a distributed architecture, where various components are situated remote from one another but may be accessed by the processor 205.

The instructions in memory 210 may include one or more separate programs, each of which comprises an ordered listing of executable instructions for implementing logical functions. In the example of FIG. 2, the instructions in the memory 210 include a suitable operating system (OS) 211. The operating system 211 essentially may control the execution of other computer programs and provides scheduling, input-output control, file and data management, memory management, and communication control and related services.

Additional data, including, for example, instructions for the processor 205 or other retrievable information, may be stored in storage 220, which may be a storage device such as a hard disk drive or solid state drive. The stored instructions in memory 210 or in storage 220 may include those enabling the processor to execute one or more aspects of the systems and methods of this disclosure.

The system 100 may further include a display controller 225 coupled to a user interface or display 230. In some embodiments, the display 230 may be an LCD screen. In other embodiments, the display 230 may include a plurality of LED status lights. In some embodiments, the system 100 may further include a network interface 260 for coupling to a network 265. The network 265 may be an IP-based network for communication between the system 100 and an external server, client and the like via a broadband connection. In an embodiment, the network 265 may be a satellite network. The network 265 transmits and receives data between the system 100 and external systems. In some embodiments, the network 265 may be a managed IP network administered by a service provider. The network 265 may be implemented in a wireless fashion, for example, using wireless protocols and technologies, such as WiFi, WiMax, satellite, or any other. The network 265 may also be a packet-switched network such as a local area network, wide area network, metropolitan area network, the Internet, or other similar type of network environment. The network 265 may be a fixed wireless network, a wireless local area network (LAN), a wireless wide area network (WAN) a personal area network (PAN), a virtual private network (VPN), intranet or other suitable network system and may include equipment for receiving and transmitting signals.

Figure 5:
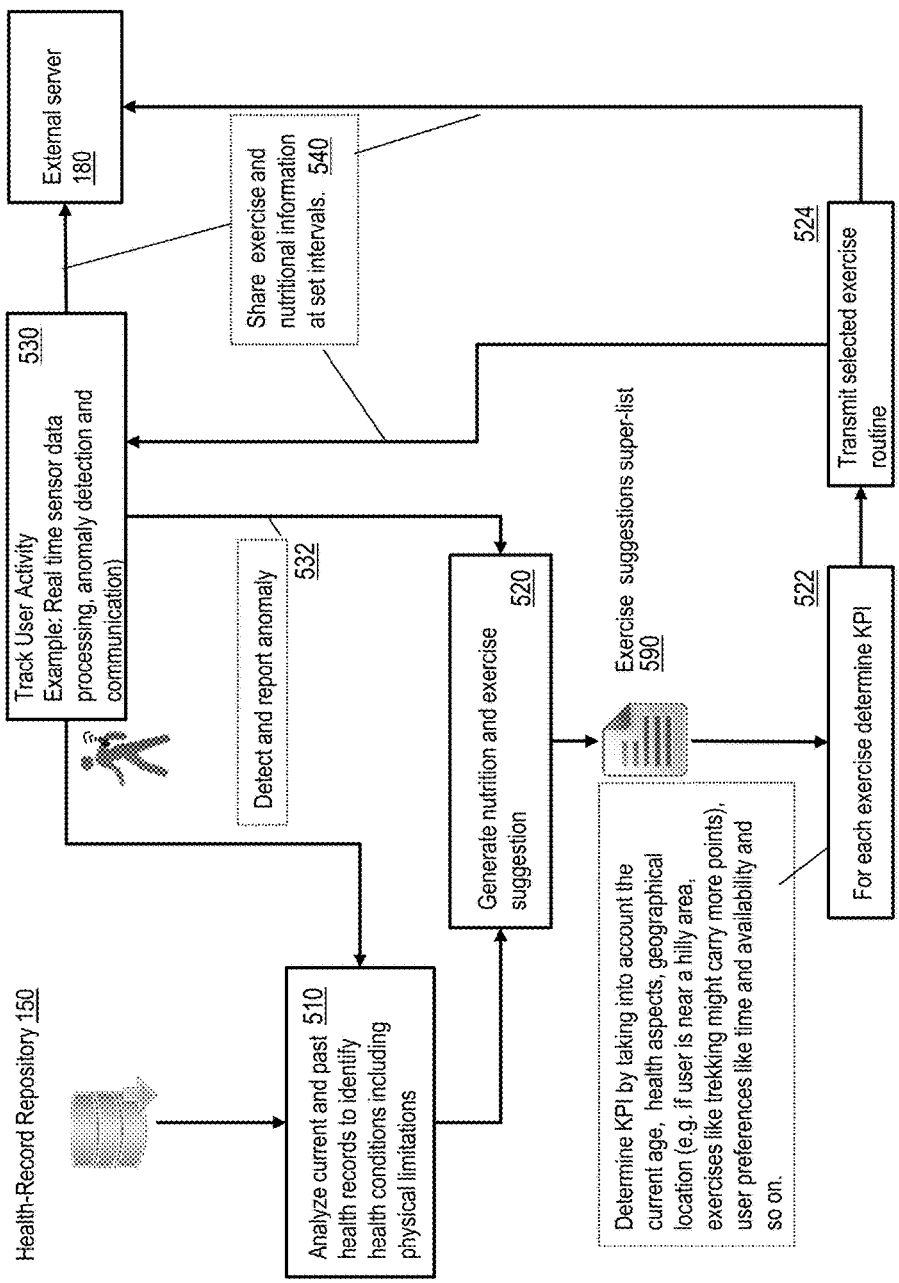
FIG. 5 illustrates a flowchart of an example method for monitoring the health of a user by a healthcare system in accordance with one or more embodiments.

FIG. 5 illustrates a flowchart of an example method for monitoring the health of the user 105 by the healthcare system 100. The health-record analyzing unit 110 analyzes the current and past health records of the user 105 and identifies current health conditions of the user 105, including physical limitations, as shown at block 510. For example, as described herein, the health-record analyzing unit 110 identifies that the user 105 has had a past surgery, or some other issue with a body part, such as a joint. The healthcare-routine generator unit 120 generates a healthcare routine for the user based on the analysis from the health-record analyzing unit 110. The healthcare routine includes nutrition and exercise routine suggestions, which are personalized for the user 105 based on his/her current and past records.

In an example, generating the exercise routine suggestion includes generating a exercise suggestion super-list 590. For example, the super-list 590 includes different types of exercises that the user 105 may be able to perform based on the analysis from the health-record analyzing unit 110. Alternatively, the super-list 590 may be a predetermined list of exercises. The healthcare-routine generator unit 120 selects the exercise routine for the user 105 from the super-list 590. For example, the healthcare-routine generator unit 120 determines and/or assigns a key performance indicator (KPI) for each exercise in the super-list 590, as shown at block 522. For example, the KPI depends on the age, health conditions, geographical location, and other such parameters specific to the user 105. For example, if the user 105 is near a hilly area (location), an exercise like trekking is assigned more KPI points than an exercise such as using a treadmill or an elliptical machine.

In addition, the KPI points may depend on the health conditions and/or limitations of the user 105. For example, if the health-record analyzing unit 110 determines that the user 105 is unable to run, the healthcare-routine generator unit 120 assigns lower KPI points to exercises that involve running and instead may assign higher KPI points to lower intensity exercise, such as walking.

Further, the healthcare-routine generator unit 120 may generate an exercise suggestion for the user 105 dynamically. For example, the healthcare-routine generator unit 120 receives a location where the user 105 typically visits, such as office, a restaurant, coffee-place, or any other location. For example, the user 105 inputs the location into the healthcare system 100. The healthcare-routine generator unit 120 identifies a parking spot for the user 105 at the location that facilitates the user 105 to take at least a predetermined number of steps, by identifying the parking spot at least a predetermined distance away from the location or the location's entrance. Accordingly, as the user 105 enters the location the user 105 walks at least the predetermined distance. In one or more examples, the healthcare-routine generator unit 120 automatically enable/disable the parking suggestion and/or notification based on time of day and weather conditions. Alternatively or in addition, the healthcare-routine generator unit 120 over time learns the user's 105 exercise habits. For example, if the user 105 exercises, such as runs 5 miles, on Monday, Wednesday, and Friday, the healthcare-routine generator unit 120 refrains from notifying the user with exercise or parking suggestions on those days.

The healthcare-routine generator unit 120 may further generate a notification for the user 105 to exercise based on the activity data from the monitoring apparatus 140. In one or more examples, the healthcare-routine generator unit 120 checks the activity data for the user 105 within a predetermined interval to determine if the user 105 needs to perform an activity. For example, if the 105 user has been sedentary for the day, and if the user 105 has no known health conditions, the healthcare-routine generator unit 120 may notify the user 105 to exercise, such as to go for a run. The healthcare-routine generator unit 120 may notify the user 105 via the monitoring apparatus 140.

The KPI may further be based on user preferences like time and availability and so on. For example, if the user 105 is generally unavailable for exercise in the evening, say after 3 PM, the healthcare-routine generator unit 120 assigns lower KPI to the exercises that requires being outdoors during that evening time. It is understood that the above scenarios are exemplary and that the healthcare system 100 generates a suggestion for a different exercise, other than walking, for the user 105 based on the user's 105 health condition, location, and schedule.

The healthcare-routine generator unit 120 assigns the KPI to the exercises for the user based on sensor data from the monitoring apparatus 140. The monitoring apparatus is monitoring the activity data of the user 105, as shown at block 530. In one or more examples, the monitoring apparatus 140 continuously monitors the activity data. In some other examples, the monitoring apparatus 140 monitors the activity data of the user at a predetermined intervals, such as every five minutes, every thirty minutes, or any other frequency. As described herein, the monitoring apparatus 140 monitors and reports to the healthcare system 100, Real time sensor data that includes physical activity and nutritional information of food consumed by the user 105.

Figure 6:
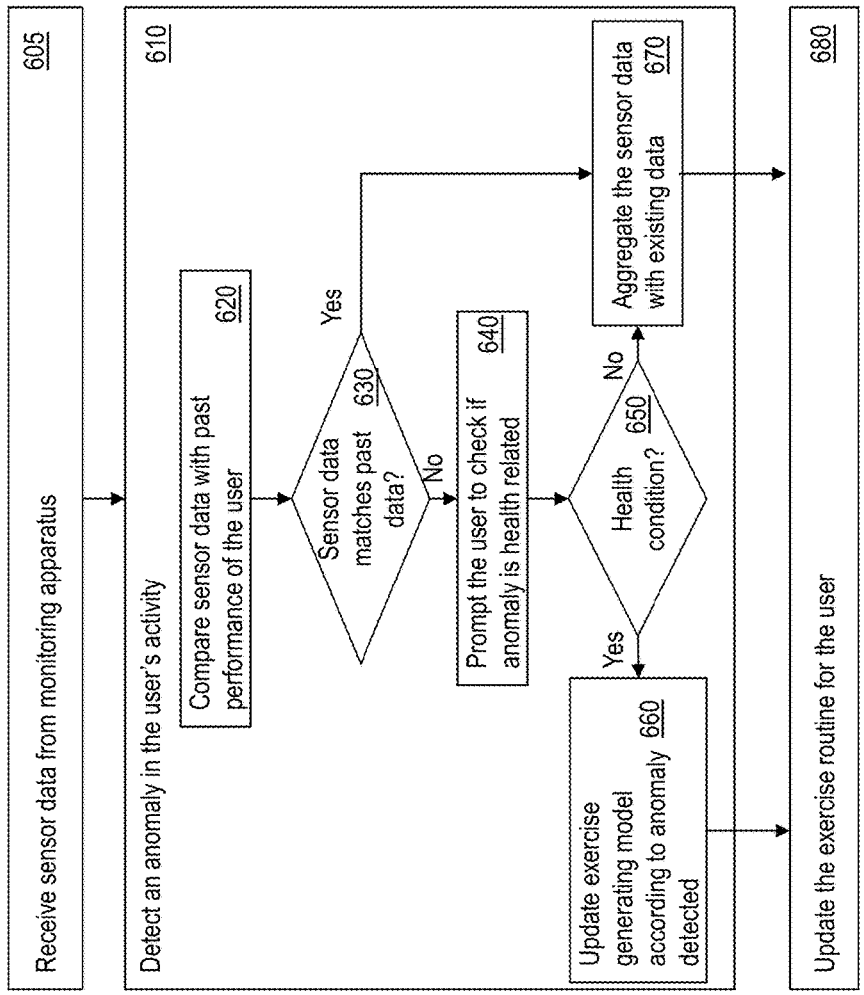
FIG. 6 illustrates a flowchart of an example method for detecting an anomaly in a user's activity and revising an exercise routine accordingly in accordance with one or more embodiments.

The monitoring apparatus 140 and/or the health-record analyzing unit upon receiving the sensor data, processes the sensor data to detect an anomaly in the user's 105 health, as shown at block 532. FIG. 6 illustrates a flowchart of an example method for detecting an anomaly in the activity of the user 105 and revising the exercise routine accordingly. The healthcare system 100, for example the health-record analyzing unit 110 receives the sensor data from the monitoring apparatus 140, as shown block 605. The health-record analyzing unit 110 detects an anomaly in the activity of the user 105, as shown at block 610. For example, the health-record analyzing unit 110 compares the sensor data with past performance of the user 105, as shown at block 620. The past performance may be determined from the health records in the health-record repository 150. If the sensor data matches the past data, the health-record analyzing unit 110 may aggregate the sensor data with the performance data, which is used for future comparisons, as shown at blocks 630 and 670. If the sensor data does not match the past data, the health-record analyzing unit 110 prompts the user 105 to check if the mismatch, that is the anomaly, is health related, as shown at block 640. In one or more examples, the health-record analyzing unit 110 prompts the user 105 if the difference between the sensor data and the past data is above (or below) a predetermined threshold. For example, if the past data indicates that the user 105 typically runs at an average pace of 10 minutes/mile, and if the sensor data indicates that the user 105 ran at a pace of 15 minutes/mile, the health-record analyzing unit 110 may prompt the user 105 to confirm that the user 105 did not experience a health-related issue (such as a fall, joint-pain, shortness of breath, an injury etc.), which resulted in the reduced pace.

For example, the prompt may be via the monitoring apparatus 140. For example, the prompt may indicate the difference in the sensor data and the past data. The prompt may facilitate the user 105 to indicate to the health-record analyzing unit 110 that the mismatch is to be ignored, for example, if the user 105 took a longer than usual break in the above example of reduced pace. In such a case, the health-record analyzing unit 110 aggregates the sensor data with existing performance data and updates the past data to be used for future comparisons, as shown at blocks 650 and 670. The prompt, alternatively or in addition, facilitates the user 105 to indicate a health condition. If the user 105 indicates of a health condition, the health-record analyzing unit 110 updates an exercise generating model, as shown at block 650 and 660. The health-record analyzing unit 110 updates the exercise routine for the user 105 based on the updated model and/or the updated performance data according to the sensor data, as shown at block 680.

Referring to FIG. 5, the healthcare system 100 transmits the generated exercise routine to the user 105 and/or other destinations such as the monitoring apparatus 140 and external server 180, as shown at block 524. In an example, the monitoring apparatus 140 and the healthcare-routine generator unit 120 share the exercise and nutritional information at set intervals with each other. Alternatively or in addition, the monitoring apparatus 140 and the healthcare-routine generator unit 120 share the exercise and nutritional information at set intervals with the external server 180. For example, the external server may be a server of an insurance provider. The insurance provider may revise an insurance premium of the user 105 based on the analysis and the tracking. Alternatively or in addition, the external server 180 may include an incentive provider server, which provides the user 105 with incentives such as monetary incentives, gifts, virtual points, rebates, or any other types of incentives for following the healthcare routine suggested by the healthcare system 100.

Figure 7:
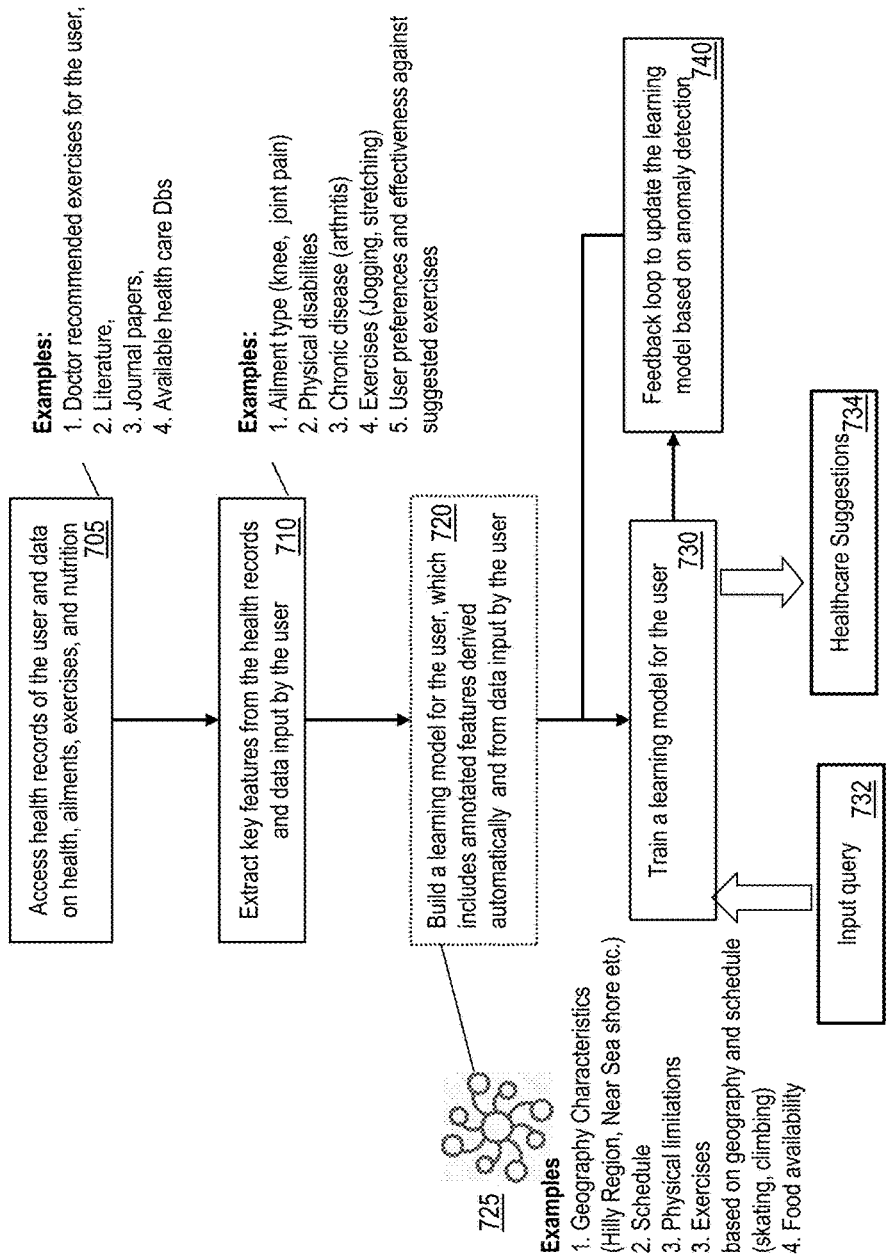
FIG. 7 illustrates a flowchart of an example method for building and training a cognitive model for a user by a healthcare system in accordance with one or more embodiments.

In one or more examples, the healthcare system 100 builds and trains a cognitive model for the user 105, which is used for suggesting the healthcare routine. FIG. 7 illustrates a flowchart of an example method for building and training a cognitive model 725 for the user 105 by the healthcare system 100. The healthcare system 100 accesses the health records of the user 105 from the health-record repository 150, as shown at block 705. The healthcare system 100 accesses data about health, ailments, exercises, and nutrition, as shown at block 705. For example, the healthcare system 100 accesses exercises recommended by a doctor for the user 105. Additionally, the healthcare system 100 accesses external healthcare databases to access literature such as journal papers. The healthcare system 100 extracts key features for the users from the health records of the user 105 and data input by the user 105, as shown at block 710. The data input by the user may include demographic information of the user 105, such as work address, home address, preferences regarding food (such as likes/dislikes specific food items such as fish, beans etc.). The healthcare system extracts features such as ailment type (knee, joint pain), physical disabilities, chronic disease (arthritis), prescribed exercises (jogging, stretching), for the user 105 from the health records and the input data.

The healthcare system 100 builds the cognitive model 725 for the user based on the extracted features. The cognitive model 725 may be based on a neural network, list learning, or other techniques. The cognitive model 525 may annotate the extracted features by automatically deriving features associated with the features from the health records and from the data input by the user 105, as shown at block 720. For example, the model 725 for the user 105 identifies that the user 105 has locations (work, or home) that is near a hilly region, near seashore, or other geographical landmarks. The cognitive model 725 further includes identities of locations to get food near the addresses associated with the user 105. Based on the model, the components of the healthcare system 100 generate the healthcare routine for the user 105. In an example, the cognitive model 725 receives an input query 732 and in response, the healthcare system 100 generates healthcare suggestion(s) 734. The healthcare system 100 additionally updates the cognitive model 725, such as using a feedback loop to modify the cognitive model 725 based on anomaly detection, as described herein, and as shown at block 740.

Figure 8:
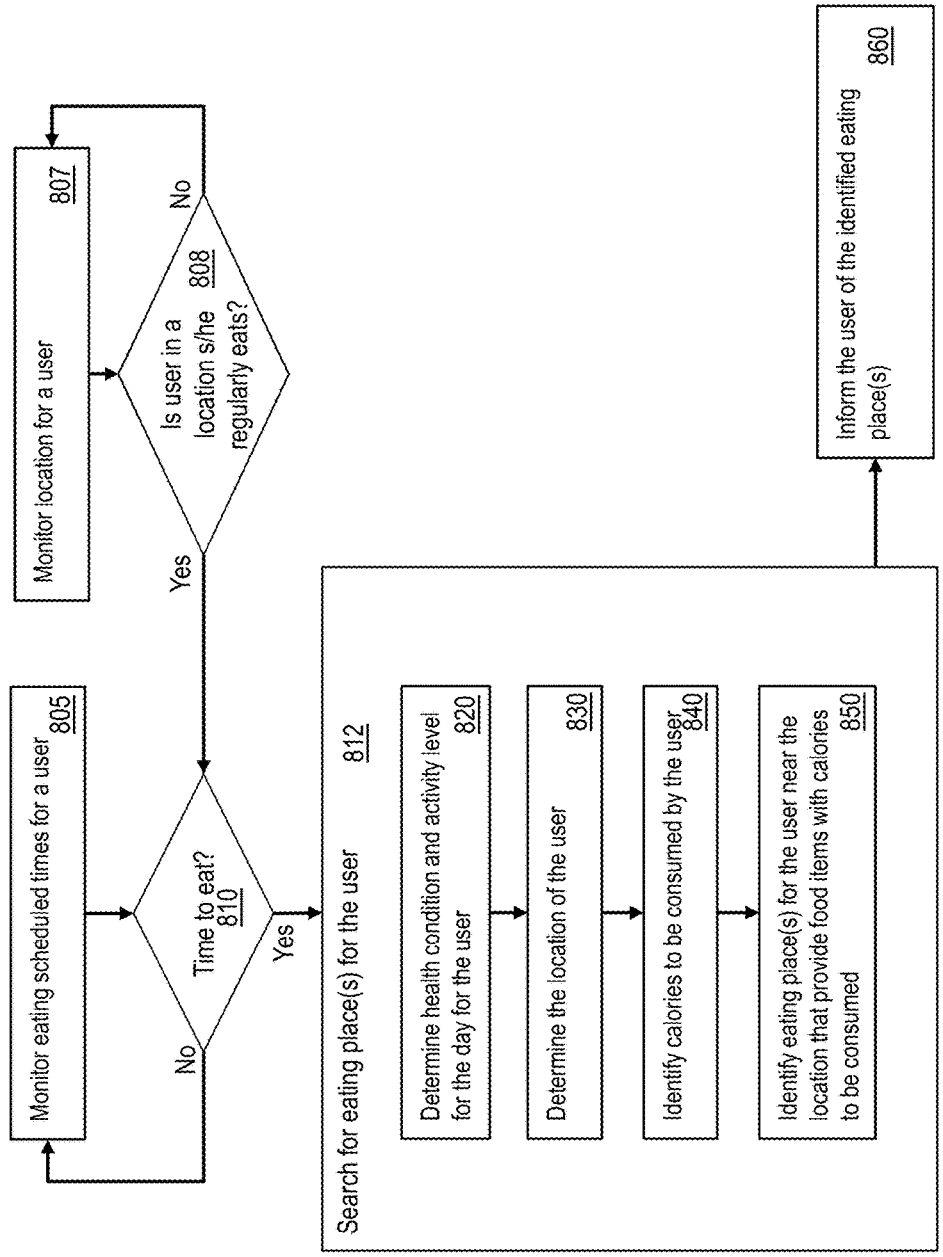
FIG. 8 illustrates a flowchart of an example method for sending a notification for an eatery to a user in accordance with one or more embodiments.

For example, the healthcare-routine generator unit 120 may suggest the user 105 where to eat based on time of day, location of the user 105, health condition of the user 105, and measured/tracked activity of the user 105 for that day. FIG. 8 illustrates a flowchart of an example method for sending a notification for an eatery to the user 105. For example, the healthcare system 100 monitors the eating schedule times for the user 105, as shown at block 805. When it is time for the user to eat according to the schedule in the healthcare routine, the healthcare system triggers a search for one or more suggested eating places for the user 105, as shown at blocks 810 and 812. In one or more examples, the healthcare system triggers the search for the one or more eating places for the user 105 in response to the user 105 entering a geographic area in which the user 105 frequently eats during the eating period (as determined by the user's 105 food tracking data), as shown at blocks 807 and 808.

The healthcare system 100 searches for eating place(s) for the user 105 based on health status and exercise done by the user 105 during that day, as shown at block 812. For example, the healthcare system 100 determines the health condition and activity level for the day for the user 105 based on the health records and the data from the monitoring apparatus 140, as shown at blocks 820 and 830. The healthcare system 100 further determines a number of calories to be consumed by the user 105 at that time according to the healthcare routine generated for the user 105, as shown at block 840. The healthcare system 100 searched for and identifies eating place(s) for the user 105 near the location that provides food items with calories to be consumed, as shown at block 850.

For example, consider that the user 105 commonly eats at a specific restaurant, however according to the activity tracking data from the monitoring apparatus 140, or from the health records, the healthcare system 100 may determine that the user 105 may have an injured leg and thus not be able to perform the exercise routine. Accordingly, the system may suggest a healthier alternative that provides food items with the required calorie amounts. In one or more examples, if the user 105 does not heed the suggestion from the healthcare system 100, the healthcare system 100 may display the amount of exercise necessary to balance out the amount of calories consumed at the specific restaurant. In one or more examples, the healthcare system 100 may generate and display a modified image of the user 105 that reflects a change in the physique of the user 105 caused by consuming the food at the specific restaurant. In one or more examples, the healthcare system may generate and display another image of the user 105 that reflects a change in the physique of the user 105 caused by consuming the food at the suggested eating place. Alternatively, if the user 105 has exercised, (for example, run 5 miles) that day, the healthcare system 100 may not provide a healthier suggestion, as described herein.

The healthcare system 100 searches a database that includes information of the eating places and their respective menus. The database may include a name, an address, a menu, calorie information of each item on the menu, an ingredient information of each item on the menu, prices of the respective menu items, user ratings for the eating place, and other such information for the eating places. The healthcare system 100 may inform the user 105 of the identified eating place(s), such as via the monitoring apparatus 140, as shown at block 860.

The healthcare system 100 continuously trains the cognitive model 725 using a feedback loop based on anomaly detected in the user's 105 activity and/or food consumption, as shown at blocks 730 and 740.

Figure 9:
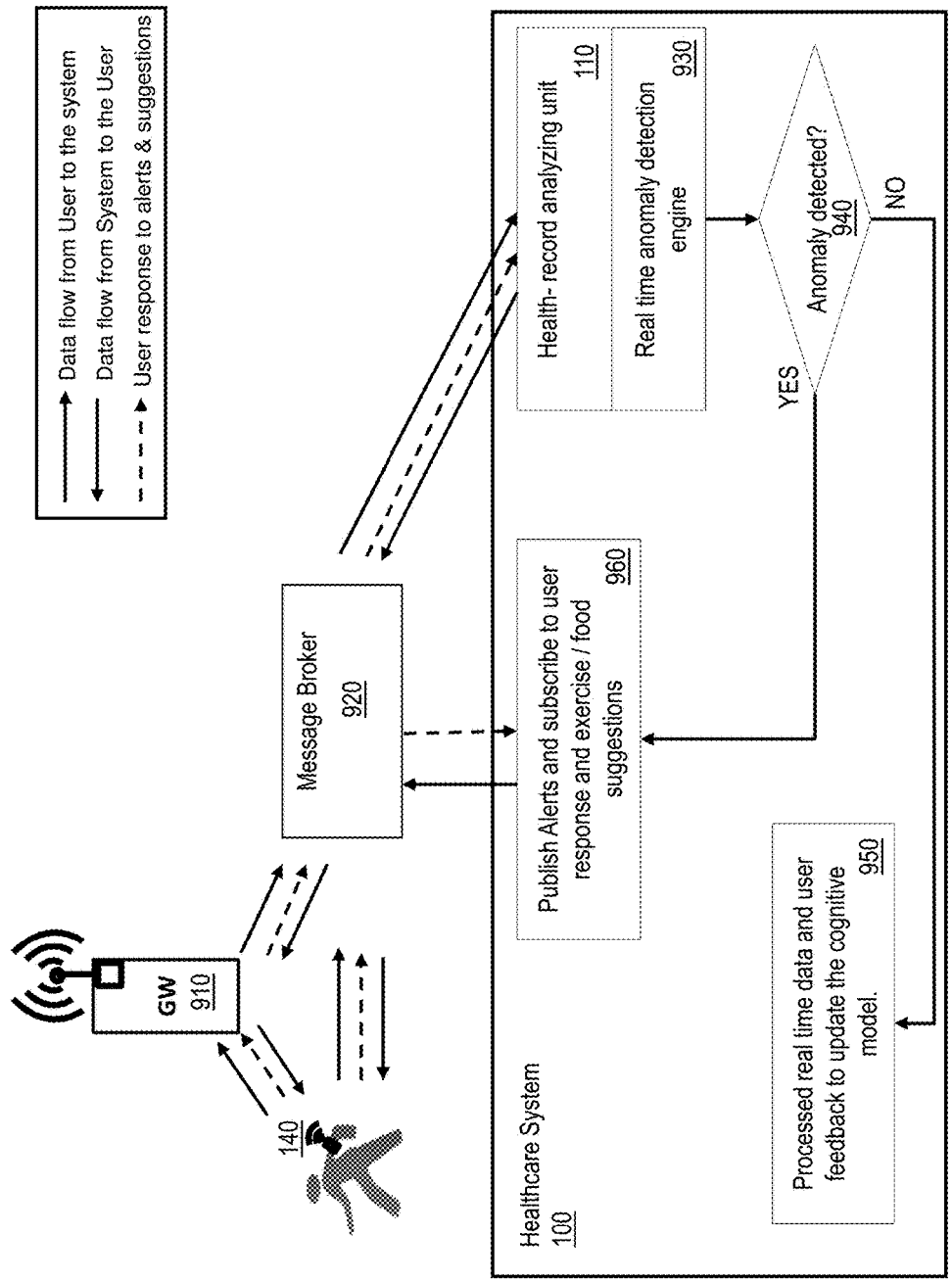
FIG. 9 illustrates a flowchart of an example method for the healthcare system to provide healthcare suggestion(s) to a user based on activity tracking data from monitoring apparatus in accordance with one or more embodiments.

FIG. 9 illustrates a flowchart of an example method for the healthcare system 100 to provide healthcare suggestion(s) to the user 105 based on activity tracking data from the monitoring apparatus 140. As illustrated, the monitoring apparatus 140 may communicate with the healthcare system 100 via a gateway 910 and/or a message broker or messaging system 920. The monitoring apparatus 140 may be a wearable device, which measures and transmits a pulse rate, a temperature, a location, a movement, a food intake (e.g. a photo of the food, manual entry of the food, or any other identifier of the food) and so on. It is understood that the communication among the components shown in FIG. 9 is illustrative, and that in other examples the components, such as the monitoring apparatus 140, may communicate directly with healthcare system 100 using, for example HTTP protocols and the like.

The gateway 910 may be an apparatus that includes components such as those illustrated in FIG. 4. The gateway 910 may include electronic circuitry and other hardware components along with computer executable instructions stored on non-transitory computer readable memory. The gateway 910 may communicate with the monitoring apparatus 140 via the network 265. The gateway 910 may further communicate with the message broker 920 via the network 265. The gateway 910 may relay communication from the monitoring apparatus 140 to the messaging system 920, and vice versa. The monitoring apparatus 140 may communicate with the gateway 910 using one or more communication protocols, such as MQTT™, CoAP™, or any other communication protocols. In an example, the gateway 910 may be an intermediate gateway such as a transparent or aggregating gateway. In one or more examples, the gateway 910 performs real time anomaly detection based on the activity tracking data from the monitoring apparatus 140. The gateway performing the analysis facilitates providing a faster response to the monitoring apparatus 140, than performing the analysis on the healthcare system 100.

In one or more examples, the monitoring apparatus 140 may communicate with the message broker 920 directly, without the gateway 910. The messaging system 920 may be an apparatus that includes components such as those illustrated in FIG. 4. The messaging system 920 may include electronic circuitry and other hardware components along with computer executable instructions stored on non-transitory computer readable memory. The messaging system 920 translates communication from the monitoring apparatus 140 into one or more protocols that the healthcare system 100 uses. Alternatively or in addition, the messaging system 920 translates communication from the healthcare system 100 into one or more communication protocols used by the monitoring apparatus 140. For example, the messaging system 920 may be a publish-subscribe message broker like MOSQUITTO™, APACHE™ KAFKA™, and so on.

The communication between the monitoring apparatus 140 and the healthcare system 100 may include a data-flow from the monitoring apparatus 140 to the healthcare system 100, such as the activity data tracked by the monitoring apparatus being sent. In addition, the communication may include data-flow from the healthcare system 100 to the monitoring apparatus 140, such as the healthcare routine and/or suggestions. Further yet, the communication may include data-flow from the user 105, via the monitoring apparatus 140, to the healthcare system 100, such as user responses in case of prompts from the healthcare system 100. The user responses may improve the anomaly detection.

In one or more examples, the monitoring apparatus 140 communicates the activity tracking data of the user 105, which is processed by the healthcare system 100, as shown at block 930. In one or more examples, the healthcare system 100 processes the activity tracking data in real time. In one or more examples, the health-record analyzing unit 110 processes the activity tracking data. The healthcare system 100 analyzes the activity tracking data to detect an anomaly, as shown at block 930.

As described herein, the methods described throughout the present disclosure may be implemented by any component of the cloud computing environment. As such, although the above scenario describes the healthcare system 100 implementing the method to provide suggestions to the user 105, the method may be implemented by one or more other components, such as the gateway 910, or the monitoring apparatus 140. In the same manner, any other method described in the present disclosure may be implemented by one or more components of the cloud environment. If an anomaly is not detected, the activity tracking data is aggregated in the user's 105 performance data to update statistical values for the user such as, averages, medians, standard deviations, variances, and other statistical values, as shown at blocks 940 and 950. In one or more examples, the healthcare system 100 updates the cognitive model 725 for the user 105 based on the computed statistical values, as shown at block 950.

If an anomaly is detected, the healthcare system 100 may prompt the user 105, and wait to receive a response from the user 105, as shown at blocks 940 and 960. In addition, in one or more examples, if the detected anomaly is above a predetermined threshold, the healthcare system 100 may publish an alert corresponding to the detected anomaly, as shown at block 960. For example, the healthcare system 100 may detect that a heartrate of the user 105 has crossed (exceeded/fallen below) a predetermined threshold, and in response publish an alert to the user 105. For example, the alert may prompt the user 105 via the monitoring apparatus 140, such as by raising an audible/visual alarm. The healthcare system 100 may detect other anomalies such as a sudden position change(fall), an abnormal pulse, an abnormal/arrhythmic heartrate, an abnormal temperature, or any other such abnormalities or a combination thereof. The healthcare system 100 may detect an abnormality by comparing the activity tracking data with past data of the user 105 from the cognitive model 725. Alternatively or in addition, the healthcare system 100 may compare the activity tracking data with typical ranges of the corresponding parameters obtained from external health databases.

The healthcare system 100 may wait for a response from the user 105 after sending an alert to confirm that the user 105 has been alerted of the detected anomaly, as shown at block 960. For example, the healthcare system 100 subscribes to the communication channel that is being used for user responses. Upon receiving a response from the user 105, confirming the anomaly, the healthcare system 100 updates the cognitive model 725 for the user 105 with information about the anomaly. In addition, the healthcare system 100 dynamically generates an exercise or dietary suggestion for the user 105 based on the anomaly detected, as described herein. The healthcare system 100 may transmit the suggestion to the user 105, for example, via the monitoring apparatus 140. The suggestion may include instructing the user 105 to stop activity, a change in activity, such as an exercise, a dietary suggestion, and the like.

Figure 10:
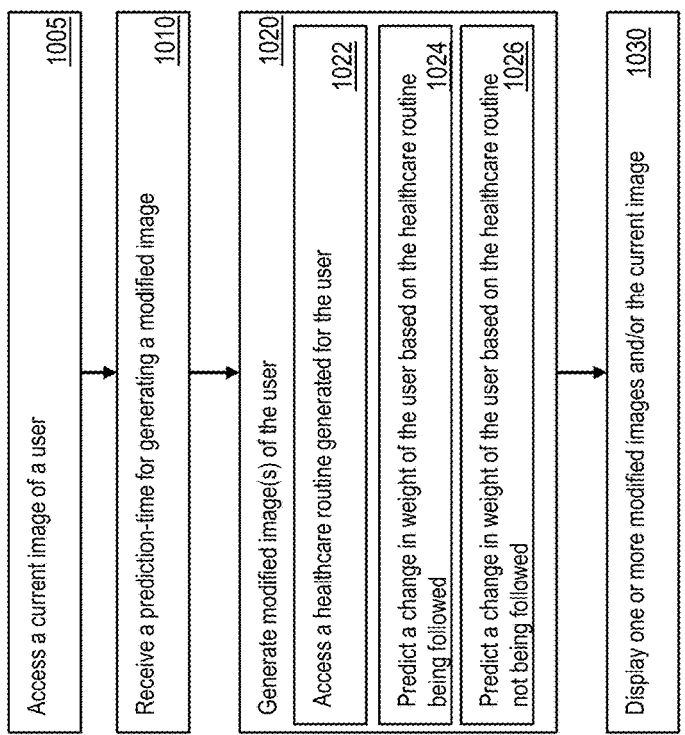
FIG. 10 illustrates a flowchart of an example method of visually portraying to a user the effects of following and/or not following a healthcare routine that a healthcare system generates for the user in accordance with one or more embodiments.

FIG. 10 illustrates a flowchart of an example method of visually portraying to the user 105 the effects of following and/or not following the healthcare routine that the healthcare system 100 generates for the user 105. The healthcare system 100 may visually portray the effects to the user 105 via the monitoring apparatus 140. In one or more examples, the healthcare system 100 may request the monitoring apparatus 140 to display the visual portrait concurrently with the healthcare routine suggestion. In one or more examples, the healthcare system 100 may provide a progress report for the user 105, which contains the visual portrayal of the user 105. The progress report may be generated and sent for viewing by the user at a predetermined schedule, such as weekly, biweekly, monthly, and so on. The user 105 may, alternatively or in addition, request the progress report from the healthcare system 100.

Visually portraying the effects of following (and/or not following) the healthcare routine includes accessing the current image 132 of the user 105, as shown at block 1005.

In one or more examples, the healthcare system 100 accesses the current image 132 by requesting the monitoring apparatus 140 to capture an image of the user 105. For example, the monitoring apparatus 140 captures the current image of the user 105 via a camera of the monitoring apparatus 140.

The healthcare system 100, specifically the image generator unit 130, receives a prediction time at which to portray the user 105, as shown at block 1010. The prediction time is a future time at which the user 105 wishes to predict the effect of the healthcare routine that the healthcare system 100 generates. For example, the prediction time may be a week, two weeks, a month, six months, in the future. In one or more examples, the user 105 may specify the prediction time by inputting a future date, or a number of days in the future from the current date, or in any other form. In response, the image generator unit 130 generates a modified image 134 of the user 105, as shown at block 1020. The modified image 134 is based on the current image 132. The image generator unit 130 may access the healthcare routine generated for the user 105 and predict a change (increase/decrease) in weight of the user 105 because of following the healthcare routine, as shown at blocks 1022 and 1024. The healthcare system 100 predicts the weight change based on change in weight of other users who followed a similar healthcare routine. The image generator unit 130 may alter the current image of the user 105 to reflect the predicted weight change and generate the modified image 134. Additionally or alternatively, the image generator unit 130 may predict a change in body composition of the user 105 and reflect the change in the body composition in the modified image 134. Access a healthcare routine generated for the user The image generator unit 130, alternatively or in addition, generates a modified image 134 based on the user 105 not following the healthcare routine, as shown at block 1026. In this regard, the image generator unit 130 predicts a weight change for the user 105 based on past health records of the user 105. The healthcare system 100 displays the one or more images, as shown at block 1030. In one or more examples, the healthcare system 100 may display the current image 132 concurrently with modified image(s) 134. Alternatively or in addition, the healthcare system 100 may store the current image 132 and the modified image 134, both images associated with two timestamps, a timestamp of the current date and a timestamp of the prediction time. The healthcare system 100 may continue to capture images of the user 105 at periodic intervals, and displaying a progress report that contains a series of captured images of the user 105 along with the predicted images of the user 105. The user 105 thus visually sees a predicted change in his/her physique because of following the healthcare routine, and at the prediction time compare the predicted image and the current image that is captured at the prediction time to verify the progress. If the progress is as predicted, the user 105 may be further motivated to follow the healthcare routine. As described herein, the healthcare system 100 may visually portray the effect of the user 105 taking a certain action, such as eating at a restaurant. In this case, the user 105 may be motivated not to take the action, such as eating at the restaurant by seeing the visual portrayal of the effect.

Figure 11:
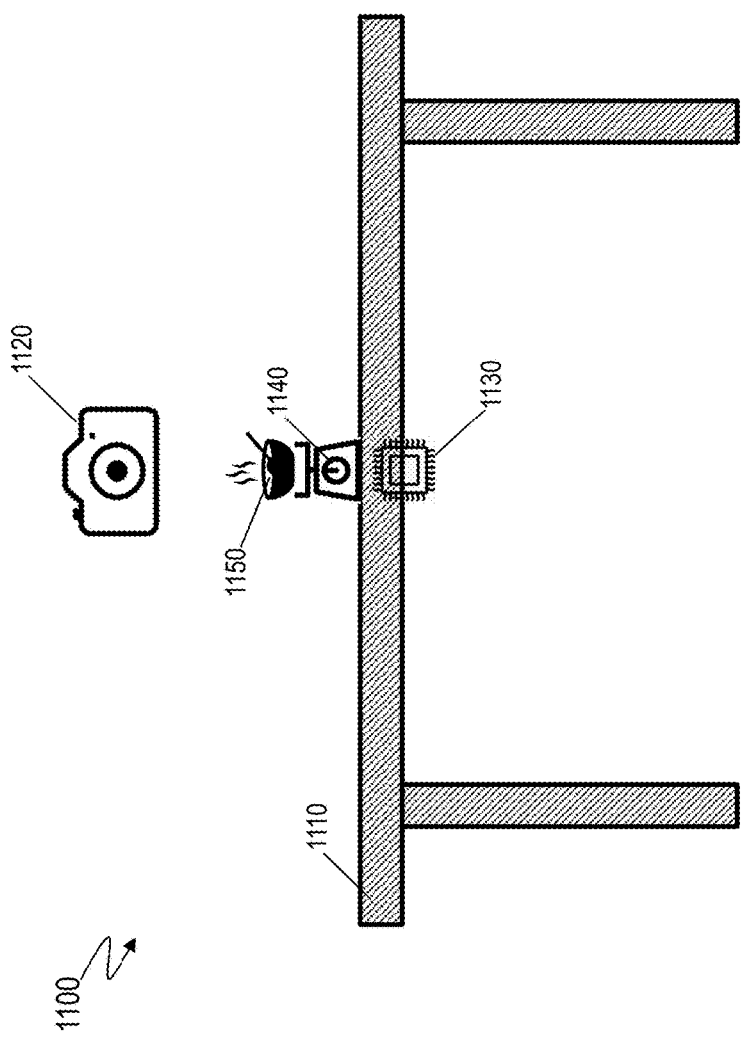
FIG. 11 illustrates an example food monitoring station in accordance with one or more embodiments.

In one or more examples, the monitoring apparatus 140 may be a food monitoring station 1100 illustrated in FIG. 11. The monitoring station 1100 includes a monitoring table 1110, a monitoring camera 1120, a food analysis unit 1130, and a weighing scale 1140, communicably coupled with each other.

The monitoring table 1110 may be a kitchen table or counter space that serves as a surface for the user 105 to prepare and/or consume a food-item 1150, such as a prepared meal. The monitoring table 1110 may serve as a conduit for communication interfaces, such as cables for the components of the monitoring station 1100, such as the monitoring camera 1120, the food analysis unit 1130, and the weighing scale 1140, among others. In one or more examples, the components of the monitoring station 1100 communicate with each other in a wireless manner, such as using WIFI™, or one or more near field communication protocols, such as ZIGBEE™, BLUETOOTH™, BLUETOOTH LOW ENERGY™, and so on.

The monitoring camera 1120 is a camera that captures an image of the food-item 1150 and/or one or more ingredients of the food-item 1150. The monitoring camera 1120 may further capture images of packaging of the food-item and/or the ingredients thereof. Alternatively, or in addition, the monitoring camera 1120 captures codes, such as barcodes, QR codes, and the like of the food-item 1150 and/or the ingredients thereof. In one or more examples, the monitoring camera 1120 may capture the images automatically upon detecting the presence of an item within a predetermined distance of the monitoring camera 1120. In one or more examples, the monitoring camera 1120 may be a multispectral camera (MSC) for estimating nutritional content and calories of the food-item 1150. In one or more examples, the monitoring camera 1120 is mounted over the monitoring table 1110, facing downwards towards the monitoring table 1110. It is understood that the monitoring camera 1120 may be installed in various other positions to capture an image of the food-item 1150. The monitoring camera 1120 communicates the captured image(s) associated with the food-item 1150 to the food analysis unit 1130.

The weighing scale 1140 measures and reports the weight of the food-item 1150. In one or more examples, the weighing scale 1140 may include a code scanner, which scans the codes of the food-item 1150 and/or the ingredients thereof. In one or more examples, the weighing scale 1140 and the monitoring camera 1120 may be part of a common unit. The weighing scale 1140 communicates the data captured by the weighing scale, such as the weight, and/or codes of the food-item 1150 to the food analysis unit 1130.

The food analysis unit 1130 analyzes an image of the food on the monitoring table 1110 captured by the monitoring camera 1120. The food-analysis unit may include the components as illustrated in FIG. 4. In one or more examples, the food analysis unit 1130 analyzes the image across various spectral bands provided by the MSC and estimates nutritional content, caloric content, food consumed, and food safety of the food. For example, the food analysis unit 1130 detects the type, or components in the food item, such as spinach based on the MSC image by processing the MSC image and using pattern recognition techniques. In one or more examples, the food analysis unit 1130 may compare one or more spectral bands in the MSC image with a known database of food properties. The food analysis unit 1130 may further display a recipe for the user 105 to follow. The user 105 may select the recipe on the food analysis unit 1130 and follow the steps as displayed. In addition, or alternatively, the user 105 may input data to the food analysis unit 1130, such as the steps being performed. The user 105 may enter the information via voice input, keyboard input, touchscreen input, or any other input technique or a combination thereof.

In one or more examples, the food analysis unit 1130 may annotate data for the food item. For example, the data from the captured image or MSC band are annotated by deriving the annotations automatically. The annotations may be based on the recipe, the food bar codes (for example on the packaging of the ingredients), dates of purchase of the food-item and/or the ingredients, cooking methods (baking, frying, roasting, grilling), and other such characteristics of the food-item or a combination thereof. In one or more examples, the food analysis unit 1130 may prompt the user 105 to input one or more of the above characteristics of the food-item 1150. In one or more examples, the food analysis unit 1130 may include, a cognitive element that learns to predict the annotations and other derived quantities about the food-item 1150 from image analytics used to process the MSC images.

The weighing scale 1140 may further capture the weight of the food-item 1150 before after the user 105 has eaten the food-item 1150. Accordingly, the weighing scale 1140 facilitates estimating total food weight consumed by the user 105 by subtracting the weight on the table after the meal from the weight before the meal.

Accordingly, the monitoring station 1100 facilitates the user 105 to determine the weight and the composition, such as the nutritional, and calorie information of the food-item 1150. The monitoring station 1100 may report the information about the food-item 1150 to the healthcare system 100 via the network 265. The healthcare system 100, as described herein, uses the information from the monitoring station 1100 in conjunction with other monitoring apparatus, such as a wearable or any other activity tracker of the user 105, to generate the healthcare routine and/or other dynamic activity suggestions for the user 105.

The health-record analyzing unit 110 of the healthcare system 100 may include a cognitive nutritional manager, which trains the cognitive model 725 of the user based on the consumption of food by the user 105, and/or the entire family of the user 105. The cognitive nutritional manager predicts weight changes of the user 105 and his/her family members based on the analysis of the food being consumed from the monitoring station 1100. As described herein the cognitive model continuously updates, and learns, such that each time the weight of the user 105 is measured, an estimated weight is compared to the actual weight. The predicted weight is based on the characteristics of the food consumed, such as the food measurements (see above) to estimate caloric intake (CI), physical activity measurements (such as from wearable monitoring apparatus) to estimate caloric outtake (CO), and a metabolic model of the user 105. The metabolic model may be parameterized based on learning user specific transformation of the difference between the calorie outtake and calorie intake (CO-CI) into a change in weight of the user 105. The healthcare system 100 also takes inputs from measurements of body mass index (BMI), muscle/fat composition, and other medical data to further estimate the expected weight changes of the user 105 on a periodic basis, such as daily, weekly, and so on. Estimates of muscle/fat composition and BMI may also be projected into the future to give the user 105 a sense of not only where the user 105 is today, but also where they will end up if the current routine of physical activity and/or food consumption is continued. The estimates in conjunction with the visual portrayal as described herein facilitates the user 105 to stay encouraged and motivated throughout the healthcare routine, which includes an exercise and diet program, by facilitating the user 105 to recognize the implications of the current routine (without following the healthcare routine).

Figure 12:
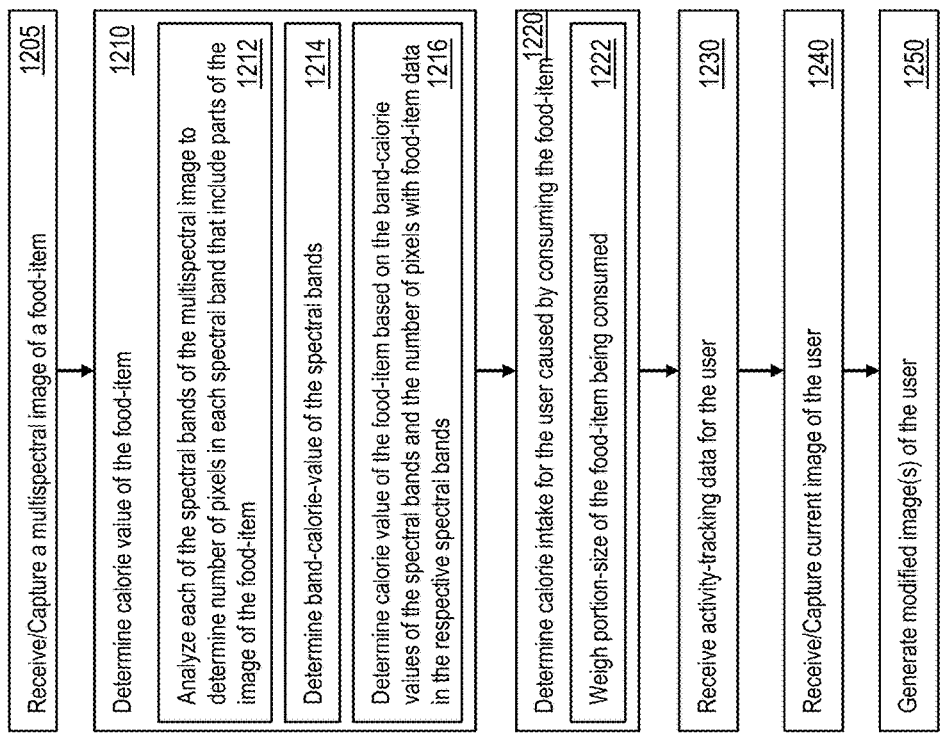
FIG. 12 illustrates a flowchart of an example method implemented by a monitoring station for monitoring the health of a user in accordance with one or more embodiments.

In one or more examples, the monitoring station 1100 implements the one or more methods described herein by receiving activity tracking data from one or more wearable computing devices. FIG. 12 illustrates a flowchart of an example method implemented by the monitoring station 1110 for monitoring the health of the user 105.

The monitoring station 1100 receives or captures a multispectral image of the food-item 1150, as shown at block 1205. In one or more examples, the food analysis unit 1130 may instruct the monitoring camera 1120 to capture the multispectral image. In one or more examples, the food analysis unit 1130 may instruct the capture in response to detecting that the food-item 1150 is being placed in a predetermined location, such as a location that can be captured by the monitoring camera 1120. Alternatively or in addition, the predetermined location may be the weighing scale 1140. Alternatively or in addition, the predetermined location may be a marked area on the table 1110.

The food analysis unit 1130 determines a caloric-value of the food-item 1150 based on the multispectral image of the food-item 1150, as shown at block 1210. In one or more examples, for determining the caloric-value, the food analysis unit 1130 analyzes each spectral band of the multispectral image, as shown at block 1212. For example, the food analysis unit 1130 may determine a number of pixels in each spectral band that include parts of the image of the food-item 1150, as shown at block 1212. The food analysis unit 1130 further determine band-caloric-values of the respective spectral bands, as shown at block 1214.

For example, each spectral band that the monitoring camera 1120 is configured to capture is assigned a predetermined band-calorie value. In one or more examples, the food analysis unit 1130 assigns the predetermined band-calorie values to the respective spectral bands of the monitoring camera 1120. The spectral bands may include one or more of a blue band (450-515/520 nm), a green band (515/520-590/600 nm), a red band (600/630-680/690 nm), a near infrared band (750-900 nm), a mid-infrared band (1550-1750 nm), a far-infrared band (2080-2350 nm), a thermal infrared band (10400-12500 nm), or other spectral bands. The monitoring station 1100 assigns each spectral band a corresponding band-caloric-value depending on the ingredients that each spectral band captures. For example, a first spectral band may be configured to capture fat content of the food-item 1150, which may be more calorie-rich than carbohydrate content of the food-item 1150 that is captured by a second spectral band. Accordingly, the first spectral band may be assigned a band-caloric-value that is higher than the band-caloric-value of the second spectral band.

The food analysis unit 1130 determines the calorie value of the food-item 1150 based on the band-caloric-values of the spectral bands and the number of pixels with food-item data in the respective spectral bands, as shown at block 1216. For example, the more the number of pixels in a spectral band, the more the content of the corresponding type in the food-item 1150. Accordingly, the food analysis unit 1130 determines a part of the caloric-value of the food-item 1150 by analyzing each spectral band. The food analysis unit 1130 determines the caloric-value of the food-item 1150 by combining the parts of the caloric-value determined from each spectral band, for example by adding the parts from each spectral band.

Further, the food analysis unit 1130 determines calorie intake for the user 105 caused by consuming the food-item 1150, as shown at block 1220. For example, the food analysis unit 1130 instructs the weighing scale 1140 to measure the weight of the portion of the food-item 1150 being consumed by the user 105, as shown at block 1222. The food analysis unit 1130 determines the calorie intake by the portion of the food-item 1150 based on the caloric-value of the food-item 1150 and the weight of the portion. In addition or alternatively, as described herein, the caloric-value of the food-item 1150 may be determined by scanning the food-label or any other identifier of the food-item 1150. The monitoring station 1100 thus determines the calorie-intake (CI) value for the user 105 by monitoring the food-item 1150 being consumed by the user.

Further, the monitoring station 1100 receives activity-tracking data for the user 105 from the monitoring apparatus 140, such as the wearable computing devices of the user 105, as shown at block 1230. The caloric-value associated with the activity-tracking data determines the calorie-outtake (CO) of the user 105. The monitoring station 1100 predicts the change in the health of the user 105, such as a change in weight, BMI, or any other health parameter of the user 105 based on the calorie-intake and calorie-outtake values. The monitoring station 1100 uses the prediction to Generate modified image(s) of the user 105 from a receive/captured current image of the user 105, as described herein, and as shown at blocks 1240 and 1250. For example, the modified images reflect a change in the weight of the user 105 compared to the current image of the user 105. The monitoring station 1100 displays the modified image(s) and/or the current image of the user 105.

In one or more examples, the monitoring station 1100 operates in conjunction with the health monitoring system 100 to display the image(s) of the user 105. For example, instead of the monitoring station 1100 predicting changes and generating the images, the monitoring station 1100 transmits the determined caloric-value of the food-item 1150 to the health monitoring system 100. The health monitoring system 100, in response, predicts the change in the health of the user 105, generates the modified image(s), and sends the image(s) to the monitoring station 1100 to display.

The technical solutions described herein uses monitoring apparatus, such as wearable sensors to determine exercise-ability, suggest exercises based on a variety of factors and shares exercise information with healthcare providers. In one or more examples, the healthcare provider, such as an insurance provider, may use the data to determine an insurance premium for one or more users. Using cognitive systems, the technical solutions describe analyzing user healthcare records. The analysis can be used to determine if the user is overweight and/or has limitations such as physical disabilities or health conditions that may impact ability to perform certain exercises. For example, if the user's health record indicates they have complained of knee or leg problems, the technical solutions prevent proposing running as an activity for the user. The technical solutions further use wearables devices such as watches and fitness bands of the user to track activity of the user continuously, such as throughout the day. The information from the monitoring apparatus is analyzed in real-time. The analysis of the data from the wearables may be used to detect abnormal movement styles that may indicate an injury. If an injury is detected, the user may be prompted to confirm. The injury is taken into account to suggest a different activity for the user. Further, alert may be issued in response to detecting the abnormal movement. Further, the technical solutions provide monitoring apparatus that assist the user to track food intake throughout the day.

Accordingly, the technical solutions describe deducing, for instance, how an injury could translate to a food suggestion. For example, if the user normally eats a pizza at a restaurant, the system suggests a healthier alternative by taking into account the affected exercise schedule due to an injury. In another example, the system translates an injury to a parking suggestion tied to an exercise routine. The technical solutions provide such suggestions to the user based on real-time cognitive analysis of the activity data and nutrition data of the user. The technical solutions build and train a prediction model to predict weight changes of the user based on the user's health records, calorie intake, and calorie outtake, and other health parameters. The technical solutions further provide continuously monitoring and collecting the calorie intake and calorie outtake data of the user via one or more monitoring apparatus such as wearables, monitoring stations, among others. The technical solutions further facilitate motivating the user to remain on track of the exercise and diet goal by providing a visual portrait of the user to reflect his/her future predicted appearance based on the feedback from the cognitive model. Additionally, the technical solutions provide real time food and exercise suggestions based on the learned user behavior and present circumstances of the user. When suggesting exercises, the technical solutions consider the time of the day and user location to suggest the exercises. The technical solutions may further provide feedback of the user's progress with the healthcare routine to a health service provider that can help derive healthcare incentives to the user.

The present technical solutions may be a system, a method, and/or a computer program product at any possible technical detail level of integration. The computer program product may include a computer readable storage medium (or media) having computer readable program instructions thereon for causing a processor to carry out aspects of the present technical solutions.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present technical solutions may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present technical solutions.

Aspects of the present technical solutions are described herein with reference to flowchart illustrations and/or block diagrams of methods, apparatus (systems), and computer program products according to embodiments of the technical solutions. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present technical solutions. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

A second action may be said to be "in response to" a first action independent of whether the second action results directly or indirectly from the first action. The second action may occur at a substantially later time than the first action and still be in response to the first action. Similarly, the second action may be said to be in response to the first action even if intervening actions take place between the first action and the second action, and even if one or more of the intervening actions directly cause the second action to be performed. For example, a second action may be in response to a first action if the first action sets a flag and a third action later initiates the second action whenever the flag is set.

To clarify the use of and to hereby provide notice to the public, the phrases "at least one of <A>, <B>, . . . and <N>" or "at least one of <A>, <B>, . . . <N>, or combinations thereof" or "<A>, <B>, . . . and/or <N>" are to be construed in the broadest sense, superseding any other implied definitions hereinbefore or hereinafter unless expressly asserted to the contrary, to mean one or more elements selected from the group comprising A, B, . . . and N. In other words, the phrases mean any combination of one or more of the elements A, B, . . . or N including any one element alone or the one element in combination with one or more of the other elements which may also include, in combination, additional elements not listed.

It will also be appreciated that any module, unit, component, server, computer, terminal or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Such computer storage media may be part of the device or accessible or connectable thereto. Any application or module herein described may be implemented using computer readable/executable instructions that may be stored or otherwise held by such computer readable media.

The descriptions of the various embodiments of the present technical solutions have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was

What is claimed is:

1. A system for monitoring a health of a user, the system comprising:
an image capture device configured to capture multispectral images;
a memory; and
a processor coupled with the memory and the image capture device, wherein the processor is configured to:
in response to an occurrence of a scheduled activity time of the user:
determine a geographic location of the user; and
select a first exercise routine for the user from a list of exercise routines that is specifically populated for the user based on a health record of the user, the first exercise routine is selected based on a key performance indicator of the first exercise routine being the maximum among the exercise routines from the list of exercise routines, the key performance indicator based on the geographic location;
receive activity-tracking data of the user from a wearable computing device;
determine a calorie outtake of the user based on the activity-tracking data, which includes calories used for the first exercise routine;
in response to an occurrence of a scheduled eating time of the user:
determine a geographic location of the user;
determine a number of calories to be consumed by the user based on the calorie outtake of the user; and
identify an eating place for the user within a predetermined vicinity of the geographic location, the eating place serving a food-item with the number of calories to be consumed by the user;
capture a multispectral image of a food-item;
determine a caloric-value of the food-item based on the multispectral image of the food-item;
output the caloric-value of the food-item as calorie-intake of the user;
access a current image of the user that comprises a picture of a body of the user;
generate a modified image of the user, wherein the modified image of the user reflects a predicted change in the body of the user based on the calorie-intake caused by consuming the food-item using a metabolic model of the user based on health records of the user; and
display the modified image of the user.

2. The system of claim 1, further comprising a weighing scale, and wherein the processor is further configured to:
measure a weight of the food-item via the weighing scale; and
determine a calorie-intake of the user based on the weight and caloric-value of the food-item.

3. The system of claim 1, wherein the processor is further configured to assign a band-caloric-value to each spectral band of the multispectral image of the food-item.

4. The system of claim 3, wherein the processor is further configured to:
extract a spectral band in the multispectral image of the food-item;
determine a number of pixels with data in the extracted spectral band; and
determine the caloric-value of the food-item based on the number of pixels and the band-caloric-value assigned to the extracted spectral band.

5. The system of claim 1, further comprising a communication interface, and wherein the processor is further configured to:
receive activity-tracking data of the user from a wearable computing device via the communication interface; and
generate the predicted change in the body of the user based on the caloric-value of the food-item and a caloric-value of the activity-tracking data.

6. The system of claim 1, wherein the predicted change is determined using a metabolic model of the user based on health records of the user.

7. The system of claim 6, wherein the predicted change is determined by the metabolic model further based on present measurements of the user comprising a body mass index and a muscle/fat composition of the user.

8. The system of claim 6, wherein the predicted change is determined by the metabolic model further based on present habits of the user comprising smoking, alcohol consumption, sun exposure, and stress.

9. A computer program product for monitoring a health of a user, the computer program product comprising a non-transitory computer readable storage medium, the computer readable storage medium comprising computer executable instructions, wherein the computer readable storage medium comprises instructions to:
in response to an occurrence of a scheduled activity time of the user:
determine a geographic location of the user; and
select a first exercise routine for the user from a list of exercise routines that is specifically populated for the user based on a health record of the user, the first exercise routine is selected based on a key performance indicator of the first exercise routine being the maximum among the exercise routines from the list of exercise routines, the key performance indicator based on the geographic location;
receive activity-tracking data of the user from a wearable computing device;
determine a calorie outtake of the user based on the activity-tracking data, which includes calories used for the first exercise routine;
in response to an occurrence of a scheduled eating time of the user:
determine a geographic location of the user;
determine a number of calories to be consumed by the user based on the calorie outtake of the user; and
identify an eating place for the user within a predetermined vicinity of the geographic location, the eating place serving a food-item with the number of calories to be consumed by the user;
capture a multispectral image of a food-item;
determine a caloric-value of the food-item based on the multispectral image of the food-item; and
output the caloric-value of the food-item as calorie-intake of the user;
determine a calorie-outtake of the user based on monitored physical activity of the user;
access a current image of the user that comprises a picture of a body of the user;
generate a modified image of the user using a metabolic model of the user, wherein the modified image of the user reflects a predicted change in the body of the user based on a difference in the calorie-intake caused by consuming the food-item and the monitored physical activity of the user, the metabolic model determines the predicted change using current measurements of a body mass index and a muscle/fat composition of the user and empirical health records of the user; and
display the modified image of the user.

10. The computer program product of claim 9, the computer readable storage medium further comprising computer executable instructions to:
measure a weight of the food-item; and
determine the calorie-intake of the user based on the weight and caloric-value of the food-item.

11. The computer program product of claim 9, the computer readable storage medium further comprising computer executable instructions to:
receive the monitored physical activity data of the user from a wearable computing device.

12. The computer program product of claim 9, wherein the computer readable storage medium further comprises computer executable instructions to assign a band-caloric-value to each spectral band of the multispectral image of the food-item.

13. The computer program product of claim 12, wherein the computer readable storage medium further comprises computer executable instructions to:
extract a spectral band in the multispectral image of the food-item;
determine a number of pixels with data in the extracted spectral band; and
determine the caloric-value of the food-item based on the number of pixels and the band-caloric-value assigned to the extracted spectral band.

14. The computer program product of claim 9, wherein the predicted change is determined by the metabolic model further based on present habits of the user comprising smoking, alcohol consumption, sun exposure, and stress.

15. A computer-implemented method for monitoring a health of a user, the method comprising:
in response to an occurrence of a scheduled activity time of the user:
determining a geographic location of the user; and
selecting a first exercise routine for the user from a list of exercise routines that is specifically populated for the user based on a health record of the user, the first exercise routine is selected based on a key performance indicator of the first exercise routine being the maximum among the exercise routines from the list of exercise routines, the key performance indicator based on the geographic location;
receiving activity-tracking data of the user from a wearable computing device;
determining a calorie outtake of the user based on the activity-tracking data, which includes calories used for the first exercise routine;
in response to an occurrence of a scheduled eating time of the user:
determining a geographic location of the user;
determining a number of calories to be consumed by the user based on the calorie outtake of the user; and
identifying an eating place for the user within a predetermined vicinity of the geographic location, the eating place serving a food-item with the number of calories to be consumed by the user;
determining a caloric-value of a food-item based on a multispectral image of the food-item;
measuring a weight of the food-item;
determining a calorie-intake of the user based on the weight and caloric-value of the food-item;
determine a calorie-outtake of the user based on monitored physical activity of the user;
generating a modified image of the user, wherein the modified image reflects a predicted change in a portrait of the user caused by a difference in the calorie-intake from the food-item and the monitored physical activity of the user, the predicted change is determined using a metabolic model of the user based on health records of the user; and
displaying the modified image of the user.

16. The computer-implemented method of claim 15, further comprising assigning a band-caloric-value to each spectral band of the multispectral image.

17. The computer-implemented method of claim 16, wherein determining the caloric-value of the food-item comprises:
extracting a spectral band in the multispectral image of the food-item;
determining a number of pixels with data in the extracted spectral band; and
determining the caloric-value of the food-item based on the number of pixels and a band-caloric-value assigned to the extracted spectral band.

18. The computer-implemented method of claim 15, further comprising:
receiving monitored physical activity data of the user from a wearable computing device.

19. The computer-implemented method of claim 15, wherein the predicted change is determined by the metabolic model further based on present habits of the user comprising smoking, alcohol consumption, sun exposure, and stress.

* * * * *